(12) United States Patent
Shih et al.

(10) Patent No.: US 10,348,985 B2
(45) Date of Patent: *Jul. 9, 2019

(54) TURBULENCE-FREE CAMERA SYSTEM AND RELATED METHOD OF IMAGE ENHANCEMENT

(71) Applicant: University of Maryland Baltimore County, Baltimore, MD (US)

(72) Inventors: Yanhua Shih, Ellicott City, MD (US); Hui Chen, Baltimore, MD (US); Tao Peng, Catonsville, MD (US)

(73) Assignee: UNIVERSITY OF MARYLAND BALTIMORE COUNTY, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/270,781

(22) Filed: Sep. 20, 2016

(65) Prior Publication Data

US 2017/0013213 A1 Jan. 12, 2017

(51) Int. Cl.
*H04N 5/359* (2011.01)
*H04N 5/372* (2011.01)
(Continued)

(52) U.S. Cl.
CPC .......... *H04N 5/3597* (2013.01); *G01N 21/41* (2013.01); *G02B 27/1066* (2013.01);
(Continued)

(58) Field of Classification Search
None
See application file for complete search history.

(56) References Cited

U.S. PATENT DOCUMENTS

| 8,242,428 B2 * | 8/2012 | Meyers | G01S 17/36 250/203.6 |
| 2009/0194702 A1 * | 8/2009 | Meyers | H04L 9/0858 250/393 |

(Continued)

OTHER PUBLICATIONS

Wen, "Forming positive-negative images using conditioned partial measurements from reference arm in ghost imaging," J. Opt. Soc. Am. A 29, 1906-1911 (2012).*

(Continued)

*Primary Examiner* — Maria E Vazquez Colon
(74) *Attorney, Agent, or Firm* — Juneau & Mitchell; Todd Juneau

(57) ABSTRACT

A turbulence-free CCD camera system with nonclassical imaging resolution, for applications in long-distance imaging, such as satellite and aircraft-to-ground based distant imaging, utilizing an intensity-fluctuation correlation measurement of thermal light. The proposed camera system has the following advantages over classic imaging technology: (1) it is turbulence-free; (2) its spatial resolution is mainly determined by the angular diameter of the light source. For example, using sun as the light source, this camera may achieve a spatial resolution of 200 micrometer for any object on Earth. 200-micrometer resolution is insignificant for short distance imaging, however, taking a picture of a target at 10-kilometer, a classic camera must have a lens of 90-meter diameter in order to achieve 200-micrometer resolution. Unlike a classic camera, the proposed turbulence-free CCD camera system has adequate spatial resolution zoom a long distance and still distinguish the objects within a small area, even with a small lens.

9 Claims, 3 Drawing Sheets

(51) Int. Cl.
   *H04N 5/217*  (2011.01)
   *H04N 5/225*  (2006.01)
   *H04N 5/235*  (2006.01)
   *G01N 21/41*  (2006.01)
   *G02B 27/10*  (2006.01)
   *G06K 9/46*   (2006.01)
   *H04N 5/232*  (2006.01)
   *G01J 1/42*   (2006.01)

(52) U.S. Cl.
   CPC ......... *G06K 9/4647* (2013.01); *H04N 5/2173* (2013.01); *H04N 5/2256* (2013.01); *H04N 5/2258* (2013.01); *H04N 5/2354* (2013.01); *H04N 5/23293* (2013.01); *H04N 5/372* (2013.01); *G01J 2001/428* (2013.01); *G01N 2021/4106* (2013.01); *G06T 2207/10032* (2013.01); *G06T 2207/30181* (2013.01)

(56) References Cited

U.S. PATENT DOCUMENTS

| 2010/0140458 | A1* | 6/2010 | Meyers | B82Y 10/00 250/214 R |
| 2011/0284724 | A1* | 11/2011 | Meyers | B82Y 10/00 250/208.1 |
| 2012/0327287 | A1* | 12/2012 | Meyers | G01B 11/24 348/335 |
| 2013/0077888 | A1* | 3/2013 | Meyers | G06T 5/50 382/274 |

OTHER PUBLICATIONS

Scarcelli et al., "Can Two-Photon Correlation of Chaotic Light Be Considered as Correlation of Intensity Fluctuations?" Phys. Rev Lett., 96, issue 6, (2006).*

* cited by examiner

TURBULENCE-FREE CAMERA SYSTEM AND RELATED METHOD OF IMAGE ENHANCEMENT

STATEMENT REGARDING FEDERALLY SPONSORED RESEARCH OR DEVELOPMENT

This invention was made with government support under FA9550-09-1-0489-2 awarded by AFOSR, and W911NF-11-2-0074 awarded by ARL. The government has certain rights in the invention.

CROSS REFERENCE TO RELATED APPLICATIONS

Provided by application data sheet in accordance with USPTO rules.

NAMES OF PARTIES TO A JOINT RESEARCH AGREEMENT

Not applicable.

SEQUENCE LISTING INCLUDED AND INCORPORATED BY REFERENCE HEREIN

Not applicable.

BACKGROUND

Field of the Invention

The invention relates to a turbulence-free camera with enhanced spatial resolution and full color reproduction.

In 1956, astrophysicists Hanbury Brown and Twiss (HBT) invented the intensity interferometer and achieved a much more accurate measurement on the angular size of distant stars. Unlike the Michelson stellar interferometer, which measures the first-order interference of electromagnetic fields at a local point, the HBT interferometer measures the second-order intensity correlation of thermal light with two independent photodetectors placed at distant space-time coordinates.

The joint-photodetection circuit outputs a nontrivial $1+(\sin x/x)^2$ correlation function while scanning the relative transverse position of the two photodetectors. When the relative transverse position close to "zero", i.e., $x\sim 0$, the intensity correlation function reaches its maximum value that is 50% greater. Taken the advantage of the intensity correlation of light coming from distant stars, HBT measured the angular diameter of the star and the angular separation between double stars that are uneasy to measure by other traditional astrophysical methods. Besides its useful applications, HBT's discovery was significant both conceptually and fundamentally. The HBT effect immediately provoked a debate on the classical or quantum nature of the phenomenon. It was this debate that stimulated the research on the basic concepts of the modern quantum theory of light. The discovery of HBT effect is a milestone in the history of modern quantum optics.

In the view of the inventors, the HBT effect is a two-photon interference phenomenon: a pair of random distributed and random radiated photons interferes with the pair itself. The two-photon interference "forces" the random photon pair to be correlated in transverse position, i.e., if one photon is observed at a position the other one has 50% more chance to be observed at a unique position simultaneously.

The HBT effect eventually spurred research into imaging technologies that take advantage of the point-to-point intensity correlation. As we understood the traditional imaging technology is based on a point-to-point correlation between the object plane and the image plane, namely the image-forming function: light coming from a point of the object plane can only be "seen" at a unique point on the image plane. In the view of the inventor, if a random pair of photons has 50% more chance to be observed at a point of the object plane and simultaneously at a unique point on a distant plane, namely the image plane, an image of the object will be obtained from a coincidence measurement of the photon pair. This thought of the inventor lead their research into the mechanism that would become known as "ghost imaging", a technique that produces an image of an object by combining information from two photodetectors: a conventional, multi-pixel detector that does not view the object (usually a CCD camera), and a "bucket" single pixel detector that does view the object, however, cannot distinguish light that coming from different points of the object.

In fact, the first experimental demonstration on ghost imaging, which was published in an 1995 article by Pittman, Shih, Strekalov, Sergienko, "Optical imaging by means of two-photon quantum entanglement," Phys. Rev. A 52 (1995), R3429, incorporated herein in its entirety, was not using thermal light. These experiments measured the coincidence of a quantum mechanically entangled photon pair, referred to as the signal and idler photon, respectively. The signal-idler pair has 100% chance to be located at a pair of two positions. In these ghost imaging experiments, after passing a lens, the signal photon either hit or passed through an object and then was detected by a bucket detector that measured only whether, but not where, the signal photon hit. At the same time, the idler photon propagated from the source directly to a CCD camera that recorded the actual position the idler photon hit. The coincidence counting rates between the bucket detector and the CCD camera were then recorded by a personal computer pixel by pixel. A 100% contrast image of the object was then observed from the coincidences.

From 2004, the inventors started to demonstrate thermal light ghost imaging by using randomly paired photons, instead of entangled photon pairs. The first a few publications includes: (1) A. Valencia, G. Scarcelli, M. D'Angelo, and Y. H. Shih, "Two-photon Imaging with Thermal Light", Phys. Rev. Lett., 94, 063601 (2005); (2) G. Scarcelli, V. Berardi and Y. H. Shih, "Can Two-Photon Correlation of Chaotic Light Be Considered as Correlation of Intensity Fluctuation?" Phys. Rev. Lett., 96, 063602 (2006); (3) R. E. Meyers, K. S. Deacon, and Y. H. Shih, "Ghost Imaging Experiment by Measuring Reflected Photons", Phys. Rev. A 77, Rapid Comm., 041801(2008). These articles are incorporated herein in its entirety. In the thermal light ghost imaging experiments, a photon either hit or passed through an object and then was detected by a bucket detector that measured only whether, but not where, that photon hit. At the same time, its random partner propagated from the source directly to a CCD array that recorded the actual position the photon hit. The CCD is placed at a distance from the light source that equals the distance between the light source and the object. The coincidence counting rates between the bucket detector and the CCD camera were then recorded by a personal computer pixel by pixel. A 50% contrast image of the object was then observed from the coincidences.

In 2011, we found and immediately demonstrated the HBT intensity correlation and thus the ghost imaging, is naturally turbulence-free. The published article by R. E. Meyers, K. S. Deacon, and Y. H. Shih, "Turbulence-free Ghost Imaging", Applied Phys. Lett., 98, 111115 (2011), is incorporated herein in its entirety.

Background of the Invention

The current state of knowledge is as follows.

Image processing is a form of signal processing for which the input is an image, such as a photograph or video frame, and the output is either image or a set of characteristics or parameters related to the image. Forms of image processing include face detection, feature detection, medical image processing, computer vision (extraction of information from an image by a computer), microscope image processing, etc.

Image resolution relates to the detail that an image possesses. For satellite images, the resolution generally correlates to the area represented by each pixel. Generally speaking, an image is considered to be more accurate and detailed as the area represented by each pixel is decreased. As used herein, the term images include digital images, film images, and/or other types of images. Classic cameras taking pictures from great distances, such as aerial photos, may not obtain detailed information about the subject matter. Consequently, subtle or detailed information are not present in the images.

When an image is captured by a monochrome camera, a single charge-coupled device (CCD) or complementary metal-oxide semiconductor (CMOS) sensor is used to form an image via the light intensity projected onto the sensor.

More specifically, "ghost imaging", especially thermal light ghost imaging, has received a great deal of attention due to the following advantages over classical imaging technology: (1) it is nonlocal, i.e., the ghost camera can "see" targets that cannot be resolved by classical cameras; (2) it is turbulence-free; and (3) its spatial resolution is mainly determined by the angular diameter of the light source.

In furtherance of the HBT effect, we have conducted an experimental study on the intensity correlation and intensity fluctuation correlations of chaotic-thermal light, further described herein, and we have demonstrated a novel technology for 100% intensity fluctuation correlation measurement of thermal light and a consequent turbulence-free imaging protocol. This protocol and the related experimentation are fully disclosed in our article 100% *Correlation of Chaotic—thermal Light*, Physical Review A. 88, Vol. 8, Issue 2, id 023808, Aug. 6, 2013, and such article is incorporated herein in its entirety.

This new protocol can be applied to produce a turbulence-free CCD camera with nonclassical imaging resolution that is determined by the angular diameter of the light source instead of that of the imaging lens. The invented camera is useful for applications in long-distance imaging, such as satellite and aircraft-to-ground based distant imaging. The proposed turbulence-free CCD camera provides all the advantages of ghost imaging to cameras used in satellite and aerial photography. For example, using sun as the light source, this camera may achieve a spatial resolution of 200 micrometer for any object on Earth at any distance without the need of a huge camera lens, because sun has a 0.53-degree angular diameter relative to Earth. 200-micrometer resolution is insignificant for short distance imaging, however, taking a picture of a target at 10-kilometer, a classic camera must have a lens of 90-meter diameter in order to achieve 200-micrometer resolution. Although a classic camera with a "small" lens may be able to "zoom" into a small area, its limited spatial resolution would not allow the classic camera to distinguish the objects within that small area.

What is needed is a camera system that can employ a small lens to take long-distance photographs that can distinguish objects within a small subject area despite atmospheric turbulence. The proposed turbulence-free required CCD camera system meets this objective.

BRIEF SUMMARY OF THE INVENTION

In a preferred embodiment, there is provided a camera system, comprising: a beam splitter receiving thermal light photons from an object or area to be imaged, each such photon passing through the beam splitter to either a CCD camera or a bucket photodetector, wherein the CCD camera passes information to a first Positive-Negative intensity fluctuation identifier (Pos-Neg identifier) and the bucket photodetector passes information to a second Pos-Neg identifier and each of the first and second Pos-Neg identifiers pass information to a positive-negative fluctuation circuit (PNFC) comprising at least one processor, at least one memory operatively associated with the processor, such memory containing a positive-negative fluctuation protocol algorithm, and wherein the PNFC detects photon coincidence from the intensity fluctuation correlation of the sunlight, and calculates the resulting correlation information for an image viewer.

In another preferred embodiment, there is provided a camera system wherein the PNFC further comprises an operatively associated detector that operates to determine the intensity of the measured light field.

In another preferred embodiment, there is provided a camera system wherein the information passed from the CCD camera and the bucket photodetector to the respective Pos-Neg identifier comprises the registration time of each photodetection event.

In another preferred embodiment, there is provided a camera system wherein the information passed from each Pos-Neg identifier to the PNFC comprises counting numbers classified as positive and negative fluctuations.

In another preferred embodiment, there is provided a camera system wherein the PNFC and associated software records the registration time of each photodetection event from the CCD camera and the bucket photodetector in two independent event timers, which are divided in to sequences of short time windows.

In another preferred embodiment, there is provided a camera system wherein the PNFC and associated software analyzes the photon counting number fluctuations in each time window, calculating the average counting numbers per short time window.

In another preferred embodiment, there is provided a camera system wherein the image produced on the image viewer is a series of images comprising a video sequence.

In a preferred method embodiment, there is provided a method of use of the camera system of claim 1, comprising the following processor implemented steps not necessarily in sequential order: providing a series of frames of a given region of interest; determining the value of each pixel at each location within each frame to form a pixel value array for each frame; summing the pixel values in each frame to obtain the frame intensity for each frame; multiplying the pixels in the pixel value array by the frame intensity to produce a frame intensity multiplied pixel value array; summing the frame intensity multiplied pixel value arrays together and dividing by the number of frames to obtain an average of the frame intensity multiplied pixel value arrays;

using the pixel value arrays, creating an array of average pixel values; determining the average frame intensity for the series of frames; multiplying the array of average pixel values by the average frame intensity for all of the inputted frames; and subtracting the array of average pixel values multiplied by average frame intensity from the average of the frame intensity multiplied pixel value arrays to provide an array of modified pixel values to form an improved image.

In another preferred embodiment, there is provided a method wherein the camera system is located on a satellite, airplane, helicopter, drone or other aerial vehicle.

In another preferred embodiment, there is provided a method wherein the thermal light photons inputted into the camera system were influenced by the effects of turbulence or adverse weather effects.

DETAILED DESCRIPTION OF THE INVENTION

Figure 1:
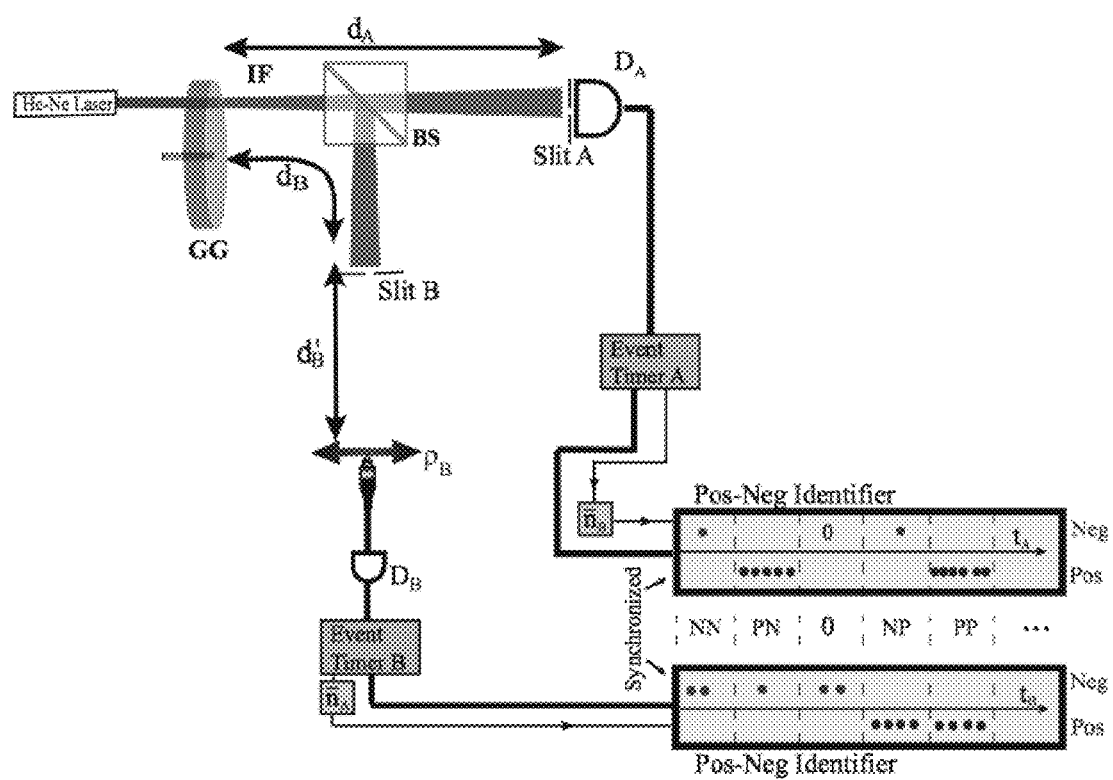
FIG. 1 is a schematic drawing of the experimental setup for studying intensity-fluctuation and second-order spatial correlation and anti-correlation by scanning point-like photodetector DA transversely.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The following terms, as used herein, have the following meanings:

A "charge-coupled device" (CCD) is a device for the movement of electrical charge, usually from within the device to an area where the charge can be manipulated, for example conversion into a digital value. This is achieved by "shifting" the signals between stages within the device one at a time. CCDs move charge between capacitive bins in the device, with the shift allowing for the transfer of charge between bins.

A "coincidence circuit" is an electronic device with one output and two (or more) inputs. The output is activated only when signals are received within a time window accepted as at the same time and in parallel at both inputs. Coincidence circuits are widely used in particle physics experiments and in other areas of science and technology.

"Photon Noise" (aka Shot noise) is a type of electronic noise which originates from the discrete nature of electric charge. The term also applies to photon counting in optical devices, where photon noise is associated with the particle nature of light.

"Ghost imaging" is a technique that produces an image of an object by combining information from two light detectors: a conventional, multi-pixel detector that does not view the object, and a single pixel (bucket) detector that does view the object.

"Type-one ghost imaging" is ghost imaging in which the imaging resolution is determined by the angular diameter, $\Delta\theta$, of the thermal source, and not by the diameters of the two imaging lenses.

"Object" means: an area, a scene, an object or objects, a landscape, overhead view of land or an object or objects, or a combination thereof.

"Frame" means: a picture, an image or one of the successive pictures on a strip of film or video.

"Process" means an algorithm, software, subroutine, computer program, or methodology.

"Algorithm" means: sequence of steps using computer software, process, software, subroutine, computer program, or methodology.

"Image sensor" means: a camera, charge coupled device (CCD), video device, spatial sensor, or range sensor. The image sensor may comprise a device having a shutter controlled aperture that, when opened, admits light enabling an object to be focused, usually by means of a lens, onto a surface, thereby producing a photographic image OR a device in which the picture is formed before it is changed into electric impulses.

"PNFC protocol" means the novel photon number fluctuation correlation measurement protocol as fully disclosed herein.

"PNFC Circuit" (PNFC) means a coincidence circuit employing the PNFC protocol.

"Processor" or "image processor" as used in the following claims includes a computer, multiprocessor, CPU, minicomputer, microprocessor or any machine similar to a computer or processor which is capable of processing algorithms.

"Operations" as used in the following claims includes steps, a series of operations, actions, processes, subprocesses, acts, functions, and/or subroutines.

"Array" refers to a systematic arrangement of data in rows and columns. An example of an array is a matrix which is a rectangular array of numbers, symbols, or expressions.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Our ghost imaging takes advantage of the nonlocal second-order point-to-point correlation of either entangled light or thermal light. In the case of thermal light, the useful point-to-point correlation is measured from the intensity fluctuations. We may call it intensity-fluctuation correlation. The intensity-fluctuation correlation of sunlight is turbulence-free, meaning it is not subject to distortion from atmospheric turbulence when traveling through the air. It is necessary to emphasize that other types of "ghost imaging" technologies may not be turbulence-free. For example, a different type of thermal light "ghost imaging" uses a so-called "speckle-to-speckle correlation" to form a "ghost" image in coincidences. In these kind experiments two sets of classical imaging systems are employed to image the speckles of the source onto the object plane and the image plane, respectively. The speckle-to-speckle correlation is produced by the first-order classical images of the speckle of the source, which is turbulence-sensitive, and thus this kind of "ghost imaging. To distinguish our ghost imaging from the speckle-to-speckle "ghost imaging", we name ours as "type-one" and the other "type-two".

In our newly developed ghost imaging process, a positive-negative fluctuation ("PNF") protocol is employed to distinguish the positive and negative intensity fluctuations of each CCD element and the bucket detector within a small time window. With this protocol, we are able to measure and calculate the correlations between positive-positive, negative-negative, positive-negative and negative-positive intensity fluctuations between the CCD and the bucket detector. This kind of correlation is referred to as "second order intensity-fluctuation correlation", and produces the ghost imaging process with a 100% contrast ghost image. This original ghost imaging process is further enhanced by the novel PNFC protocol newly disclosed herein below.

Our newly designed PNFC protocol divides the timely accumulative measurement into short time windows, $\Delta t$, and calculates the mean intensity of the measurement. The PNFC protocol is then make a positive-negation intensity-fluctuation judgment for the measured intensity within each short time window $\Delta t_j$. If the measured intensity $I_j$ is greater than the mean intensity, we name it positive-fluctuation. If the measured intensity $I_j$ is smaller than the mean intensity, we name it negative-fluctuation. With this protocol, we are able to separately record the measured positive-fluctuation and negative-fluctuation of the CCD and the "bucket" detector into two sets of sequences of short time windows $\Delta t_j$. We are thus able to calculate the intensity-fluctuation correlation between the positive-positive, negative-negative, positive-negative, and negative-positive intensity fluctuations of the CCD and the "bucket" detector. Significantly, the PNFC protocol brings us a turbulence-free 100% intensity-fluctuation correlation, which does not contain the turbulence-sensitive one-half that is indistinguishable in the traditional second-order correlation measurements of two identical classical images.

In our novel PNFC protocol, the 100% intensity-fluctuation correlation of thermal light, and the turbulence-free CCD camera have been experimentally demonstrated.

The use of intensity-fluctuation correlation for "ghost" imaging, especially sunlight "ghost" imaging, provides an avenue for enhancement of the utility of long-distance photography due to the following advantages over classical imaging technology: (1) it is nonlocal, i.e., the ghost camera can "see" targets that cannot be resolved by classical cameras; (2) it is turbulence-free; and (3) its spatial resolution is mainly determined by the angular diameter of the light source. These characteristics are especially advantageous in the areas of satellite and aerial photography.

For example, a sunlight ghost image of any object on earth may achieve a spatial resolution of 200 micrometer because the sun has an angular diameter of 0.53 degree relative to Earth. Such level of spatial resolution is insignificant for short distance imaging, but to take a picture of a target at 10 kilometers, a classical camera must have a lens 90 meters in diameter to achieve 200-micrometer resolution.

In addition to enhanced spatial resolution, the disclosed turbulence-free CCD camera system uses natural sunlight for turbulence-free distance imaging applications with full color reproduction.

The invention comprises an enhancement of ghost imaging from its classical simulation. There are currently two known types of thermal light "ghost imaging". Type-one ghost imaging, which is used in the present invention, uses the intensity-fluctuation correlation $\langle \Delta I_o \Delta I_i \rangle$, or photon number fluctuation correlation $\langle \Delta n_o \Delta n_i \rangle$, between the object-plane and the image-plane to produce the second-order image in the joint measurement between a "bucket" photodetector and a CCD array. Type-two can be considered as a classical simulation of the original ghost imaging. A type-two ghost image is produced by two sets of identical intensity distributions or the so called "speckle-to-speckle" correlation of thermal light. Mathematically, the two are easily recognized from their image-forming correlation function:

Type-One:

$$R_c(\vec{\rho}_i) = \int d\vec{\rho}_o |A(\vec{\rho}_o)|^2 \langle \Delta I_o \Delta I_i \rangle$$

$$= \int d\vec{\rho}_o |A(\vec{\rho}_o)|^2 \langle \Delta n_o \Delta n_i \rangle$$

$$= \int d\vec{\rho}_o |A(\vec{\rho}_o)|^2 somb^2 \frac{\pi \Delta \theta}{\lambda}(\vec{\rho}_0 - \vec{\rho}_i)$$

where $R_c$ is the coincidence counting rate; $\vec{\rho}_o$ and $\vec{\rho}_i$ are the transverse coordinates of the object-plane and the image-plane, respectively; $A(\vec{\rho}_o)$ is the aperture function of the object; $somb(x) = 2J_1(x)/x$ with $J_1(x)$ the first-order Bessel function and $\lambda$ the wavelength.

Type-Two:

$$R_c(\vec{\rho}_i) = \int d\vec{\rho}_o |A(\vec{\rho}_o)|^2 \langle I_o \rangle \langle I_i \rangle$$

$$= \int d\vec{\rho}_o |A(\vec{\rho}_o)|^2 \langle n_o \rangle \langle n_i \rangle$$

$$= \int d\vec{\rho}_o |A(\vec{\rho}_o)|^2 somb \frac{\pi D_o}{s_o^0 \lambda}(\vec{\rho}_s - \vec{\rho}_o/m_o)$$

$$somb \frac{\pi D_i}{s_i^0 \lambda}(\vec{\rho}_s - \vec{\rho}_i/m_i)$$

where $\vec{\rho}_s$ is the transverse coordinate of the source-plane; $D_o(D_i)$ is the diameter of the imaging lens on the object (image) side; $s_o^0(s_i^0)$ is the distance between the source to the imaging lens on the object (image) side; $m_o(m_i)$ is the magnification factor of the classical imaging system on the object (image) side. The two sorb-functions are made by two sets of classical imaging systems, which produce two sets of identical "speckles" of the source-plane onto the object-plane and the image-plane.

In a preferred embodiment, the HBT intensity correlation used in our variety of ghost imaging is naturally turbulence-free, and thus the software associated with the PNFC is not required to perform corrections.

DETAILED DESCRIPTION OF THE FIGURES

FIG. 1 schematically illustrates the photon number fluctuation correlation measurement protocol, namely the positive-negative fluctuation correlation measurement circuit (PNFC). The PNFC protocol records the registration time of each photodetection event of $D_A$ and $D_B$ in two independent "Event Timers" along their time axes $t_A$ and $t_B$, which are divided into sequences of short time windows $\Delta t_j$, $j$=A, B. The circuit and the associated software analyze the photon counting number fluctuations in each time window $\Delta t_j$. The software first calculates the average counting numbers per short time window, $\bar{n}_A$ and $\bar{n}_B$. Two virtual logic circuits ("Pos-Neg identifiers") classify the counting numbers per window as "positive" and "negative" fluctuations based on $\bar{n}_A$ and $\bar{n}_B$, $$\Delta n_{jA}=n_{jA}-\bar{n}_A; \Delta n_{jB}=n_{jB}-\bar{n}_B,$$

Where j=1 to $N_{win}$ labeling the jth short time window. $N_{win}$ is the total number of time windows in a measurement. After synchronizing the time windows of channel-A and channel-B, the fluctuation-fluctuation coincidences in the jth time window is calculated, $$R_j=\Delta n_{jA} \times \Delta n_{jB}.$$

The statistical Fluctuation-fluctuation correlation is thus calculated as follows:

$$\langle \Delta n_A \Delta n_B \rangle = \sum_j R_j = \sum_j \Delta n_{jA} \times \Delta n_{jB} \propto \langle \Delta I_A \Delta I_B \rangle.$$

Figure 2:
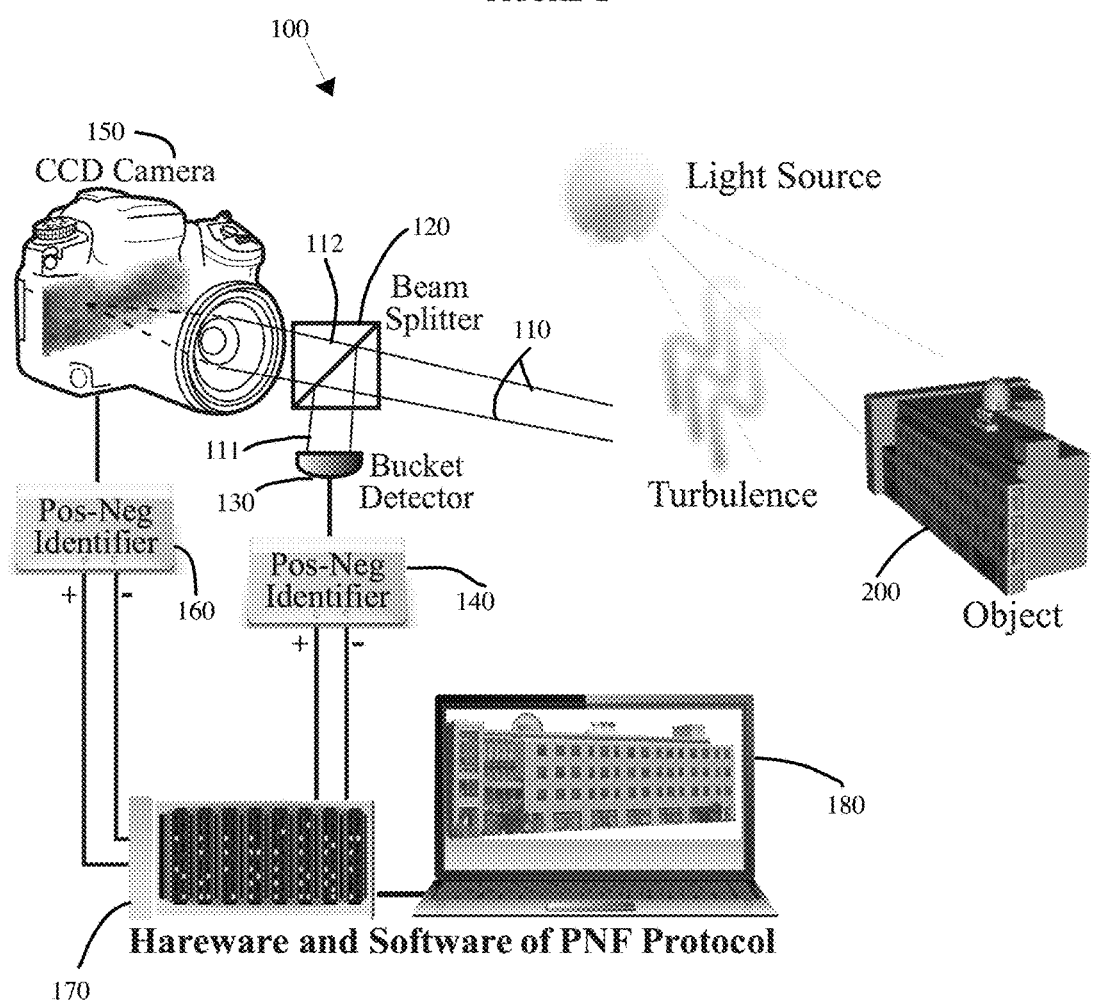
FIG. 2 is a general schematic diagram for measuring statistical correlation. In this experiment, the "observable" are the "positive" (above mean value) and "negative" (below mean value) intensity fluctuations.

FIG. 2 is a schematic drawing evidencing one embodiment of the disclosed turbulence-free camera system 100 that uses natural sunlight for turbulence-free distant imaging applications with enhanced spatial resolution and full color reproduction. In FIG. 2, correlated photons 110 pass through beam splitter 120 and are split, with split photons 111 passing to bucket photodetector 130 and thereby to Pos-Neg Identifier 140 and thereby to a PNF circuit (PNFC) 170, while split photons 112 pass to CCD Camera 150 and thereby to Pos-Neg Identifier 160 and thereby to a PNFC 170, with PNFC 170 finally passing reconstituted imaging information to final image viewing device 180.

The operations employed by camera system 100, and illustrated by FIG. 2, are as follows. CCD camera 150 takes a picture through atmospheric turbulence. The image of the target on the CCD array will be "blurred" due to the turbulence or due to the poor spatial resolution of the camera, if its imaging lens is not large enough for the distance to the imaged object 200. However, with the help of the bucket photodetector 130 and a novel coincidence detection protocol, namely the "PNF" protocol, a turbulence-free image of the target of 200 micrometer imaging resolution can be observed from the intensity fluctuation correlation measurement. The positive-negative fluctuation protocol distinguishes the positive and negative intensity fluctuations, or photon number fluctuation, of each CCD element and bucket photodetector 130 within a small time window. With the novel protocol, we are able to measure and calculate the correlations between the positive-positive, negative-negative, and negative-positive intensity fluctuations, or photon number fluctuations between the CCD camera 150 and the bucket photodetector 130. This "second order" correlation produces an image based on the coincidences.

Figure 3A:
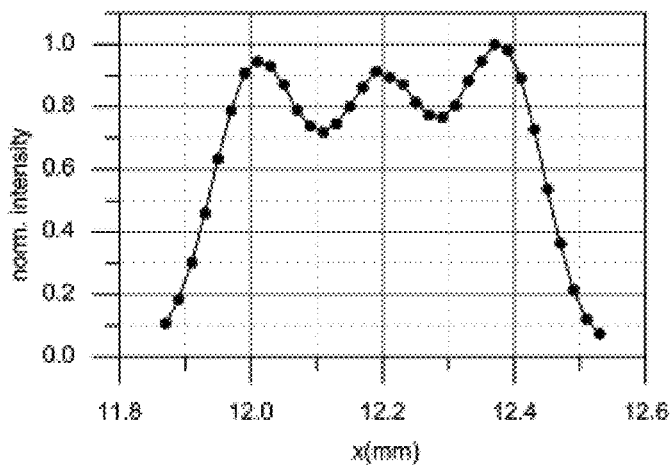
FIGS. 3A, 3B, and 3C are schematic drawings of a turbulence-free imaging system.
Figure 3B:
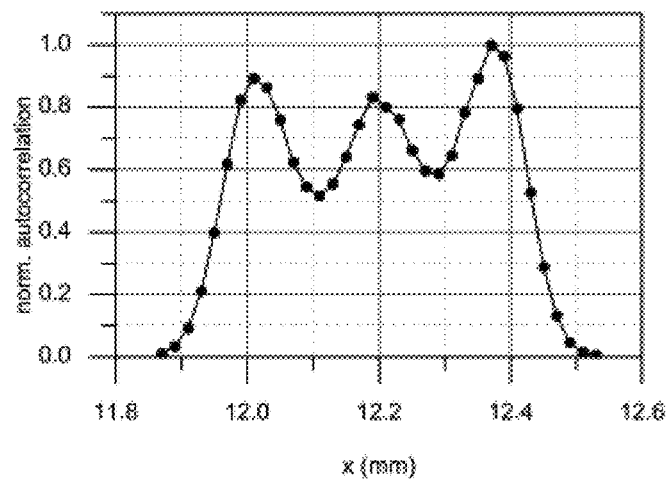
Figure 3C:
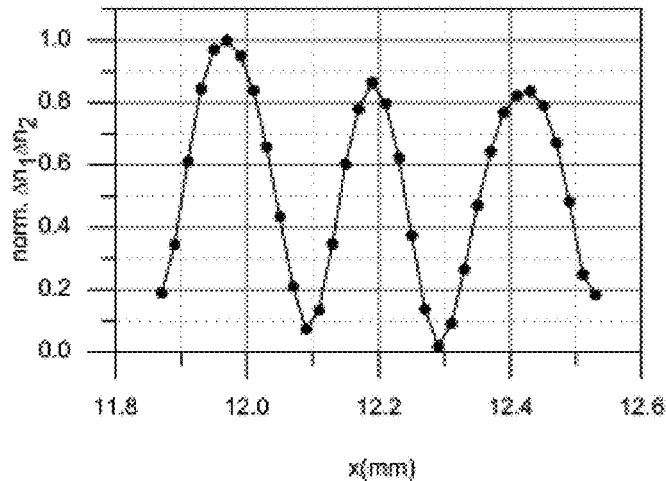

FIGS. 3(a)-(c) comprise a series of graphs indicating the spatial resolution of various types of imaging. FIG. 3(a) evidences a classical image of a spatial resolution gauge directly observed from the CCD camera. FIG. 3(b) evidences classically correlated image of the same gauge which is the result of the formula $$\langle I(\vec{\rho}_o) \rangle \langle I(\vec{\rho}_o) \rangle.$$

FIG. 3(c) evidences the image of the same gauge as FIGS. 3(a) and 3(b), but taken by the new turbulence-free ghost imaging camera system. Comparison of the graphs indicates that: the image of the classical CCD camera in FIG. 3(a) is almost invisible; the classically correlated image of FIG. 3(b) is improved (roughly a 1.414 gain), but remains blurred; while the type-one ghost image of the gauge illustrated in FIG. 3(c) remains 100% resolvable.

Example 1—Construction of Prototype Turbulence-Free CCD Camera

In this example a prototype turbulence-free CCD camera is developed that is able to take second-order turbulence-free images.

Materials

The prototype unit consists of a commercial research grade CCD camera, and hardware and software to interface with the PNFC system. Intensity fluctuation-fluctuation correlation calculations, involving large-dimensional matrix algebra, are conducted using commercial PCs and multi-crosstalk graphic cards.

CCD Camera

Based on the optical and electronic parameters of the CCD camera, the hardware parts are designed for a ghost imaging system including the PNFC system and the hardware-interface between the CCD camera and the PNFC protocol as well as coincidence-measurement circuits. This results in a working PNFC system and hardware interface between the CCD camera and the PNFC.

Multi-Crosstalk Graphic Cards

The software is developed for multi-crosstalk graphic cards for the system for the coincidence-measurement circuit and positive-negative fluctuation analysis. The production of this software results in working software for taking data from the CCD and the bucket detector, analyzing and identifying the positive-negative fluctuations, calculating the correlations between the positive-negative fluctuations, producing the ghost image from the fluctuation-fluctuation correlation.

Interface Software and Hardware

The above individual working software is then interfaced with the individual working hardware systems to produce a working ghost imaging system with the PNFC.

Testing

The constructed turbulence-free PNFC camera is then tested comparing it with a classic camera that has similar lens and zooming ability. The main test shall be the spatial resolution of the prototype system that results in a working prototype system and a testing report on its turbulence-free nature and nonclassical spatial resolution of a 200 micrometer grid at a distance of 100 m.

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

We claim:

1. A camera system, comprising: a beam splitter receiving thermal light photons from an object or area to be imaged, said thermal light photons passing through the beam splitter to either an image sensor or a bucket photodetector, wherein the image sensor passes information to a first Pos-Neg identifier and the bucket photodetector passes information to a second Pos-Neg identifier and each of the first and second Pos-Neg identifiers pass information to a positive-negative fluctuation circuit (PNFC) comprising at least one processor, at least one memory operatively associated with the processor, such memory containing a positive-negative fluctuation protocol algorithm, and wherein the PNFC detects photon coincidence from intensity fluctuation correlation of sunlight, and passes the resulting correlation information to an image viewer.

2. The camera system of claim 1 wherein the information passed from the image sensor and the bucket photodetector to the respective Pos-Neg identifier comprises a registration time of each photodetection event.

3. The camera system of claim 1, wherein the information passed from each Pos-Neg identifier to the PNFC comprises counting numbers classified as positive and negative fluctuations.

4. The camera system of claim 1 wherein the PNFC and associated software records a registration time of each photodetection event from the image sensor and the bucket photodetector in two independent event timers, which are divided in to sequences of short time windows.

5. The camera system of claim 4, wherein the PNFC and associated software analyzes photon counting number fluctuations in each short time window, calculating an average counting numbers per short time window.

6. The camera system of claim 1 wherein an image produced on the image viewer is a series of images comprising a video sequence.

7. A method of use of the camera system of claim 1, comprising the following processor implemented steps not necessarily in sequential order: providing a series of frames of a given region of interest; determining a value of each pixel at each location within each frame to form a pixel value array for each frame; summing the pixel values in each frame to obtain a frame intensity for each frame; multiplying the pixels in the pixel value array by the frame intensity to produce a frame intensity multiplied pixel value array; summing the frame intensity multiplied pixel value arrays together and dividing by the number of frames to obtain an average of the frame intensity multiplied pixel value arrays; using the pixel value arrays, creating an array of average pixel values; determining an average frame intensity for the series of frames; multiplying the array of average pixel values by the average frame intensity for the series of frames; and subtracting the array of average pixel values multiplied by average frame intensity from the average of the frame intensity multiplied pixel value arrays to provide an array of modified pixel values to form an improved image.

8. The method of claim 7, wherein the camera system is located on a satellite, airplane, helicopter, drone or other aerial vehicle.

9. The method of claim 7, wherein the thermal light photons inputted into the camera system were influenced by effects of turbulence or adverse weather effects.

* * * * *